US006689135B2

(12) United States Patent
Enayati

(10) Patent No.: US 6,689,135 B2
(45) Date of Patent: Feb. 10, 2004

(54) EXPANDABLE BONE FASTENER AND INSTALLATION TOOL

(76) Inventor: Albert Enayati, 809 Carter La., Paramus, NJ (US) 07652

( * ) Notice: Subject to any disclaimer, the term of this patent is extended or adjusted under 35 U.S.C. 154(b) by 100 days.

(21) Appl. No.: 10/057,529

(22) Filed: Jan. 25, 2002

(65) Prior Publication Data

US 2003/0144667 A1 Jul. 31, 2003

(51) Int. Cl.⁷ .............................................. A61B 17/04
(52) U.S. Cl. ......................... 606/72; 606/232; 411/21; 411/41; 411/60.1
(58) Field of Search .................... 606/72, 77, 78, 606/104, 232, 63, 66, 68; 411/21, 39, 40, 41, 46, 50, 51, 54, 60.1, 62, 70, 909; 433/173, 201.1; 623/11.11, 13.14, 16.11, 23.75

(56) References Cited

U.S. PATENT DOCUMENTS

| | | | | |
|---|---|---|---|---|
| 2,685,877 A | * | 8/1954 | Dobelle | 623/23.11 |
| 4,632,101 A | * | 12/1986 | Freedland | 606/68 |
| 4,927,287 A | * | 5/1990 | Ohkawa et al. | 403/408.1 |
| 5,360,450 A | * | 11/1994 | Giannini | 623/21 |
| 5,766,009 A | * | 6/1998 | Jeffcoat | 433/173 |
| 5,797,963 A | * | 8/1998 | McDevitt | 606/232 |
| 5,849,004 A | * | 12/1998 | Bramlet | 606/232 |
| 5,928,244 A | * | 7/1999 | Tovey et al. | 606/104 |
| 6,149,669 A | * | 11/2000 | Li | 606/232 |

* cited by examiner

Primary Examiner—Eduardo C. Robert
Assistant Examiner—David Comstock
(74) Attorney, Agent, or Firm—Michael G. Petit

(57) ABSTRACT

An expandable bone fastener adapted to be inserted into an untapped hole drilled in a bone, thereafter adapted to expand a plurality of barbs into the surrounding bone has an enlarged proximal end, a tubular outer body portion having an axial bore, a distal end having either expandable or non-expandable legs dimensioned to fit snugly within the hole, and an expansion pin slidably mounted within the axial bore. The tubular outer body portion of the expandable bone fastener has a plurality of longitudinal slots in the wall thereof to allow the expansion and retraction of the expansion pin's barbs into or out of the surrounding bone. The barbs on the expansion pin may be elastically deformed from a normal, retracted configuration to a locking, splayed configuration wherein the outer ends of the barbs extend outwardly through the slots in the tubular outer body portion to penetrate the surrounding bone as the expansion pin is moved in a proximal direction from a fully extended position. The expansion pin includes a plurality barbs located in circumferentially spaced relation about the cylindrical body of the expansion pin and positioned in various angles and positions respect to the vertical axis. In all embodiments of the expandable bone fasteners, both the tubular outer body and the expansion pin, or portions thereof, may be fabricated from bioabsorbable or non-absorbable materials, the choice of material for a particular portion of the fastener depending on the application. Hybrid embodiments are also disclosed.

8 Claims, 5 Drawing Sheets

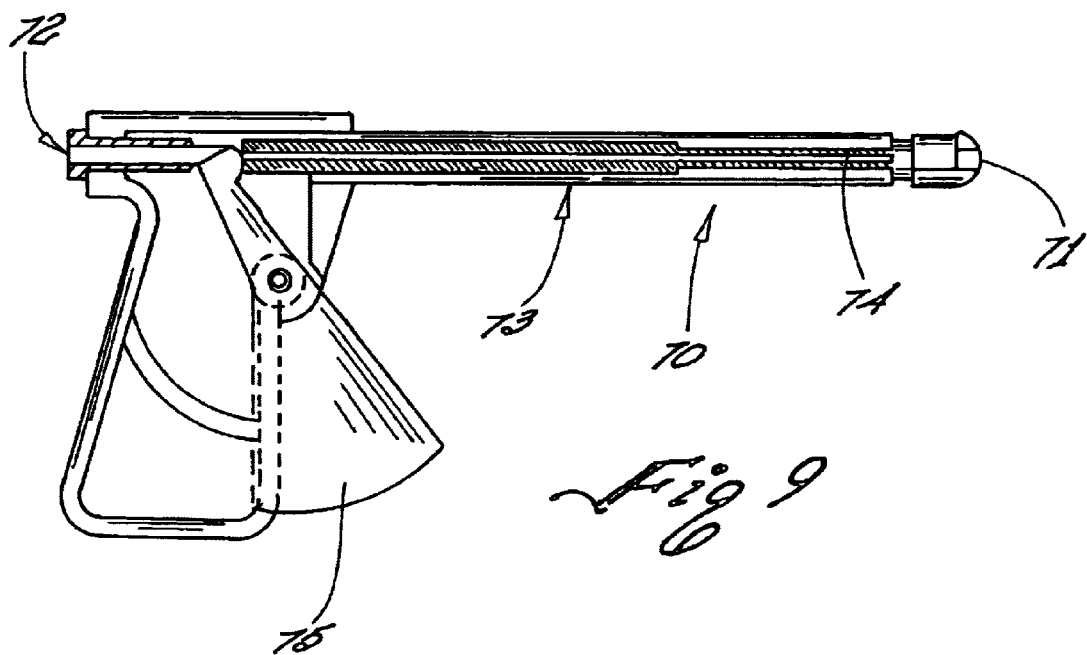
*Fig 9*
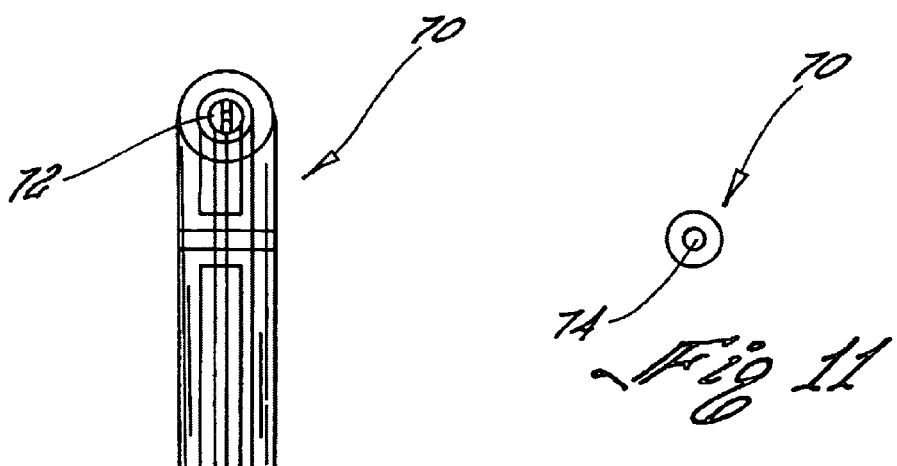
*Fig 10*   *Fig 11*
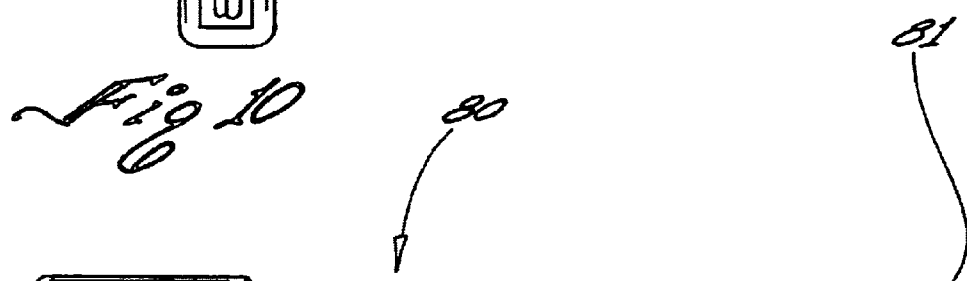
*Fig 12*

EXPANDABLE BONE FASTENER AND INSTALLATION TOOL

BACKGROUND OF THE INVENTION

1. Field of the Invention

This invention relates to fasteners for attaching a substrate to a bone, and more particularly to fasteners for anchoring soft tissue or bone plates to bone.

2. Prior Art

In U.S. Pat. Nos. 4,580,936, 4,859,128, 4,877,362, 5,030,050, 5,441,500, 5,489,210, 5,713,903, 5,968,044, 5,417,712, 5,501,695, 5,522,845, 5,571,104 and 6,290,701 there are disclosed a variety of anchors for attaching suture, bone and/or soft tissue to bone. The foregoing patents further disclose a number of installation tools for deploying the anchors disclosed therein. Complete details of the construction and operation of these anchors and their associated installation tools are provided in the above-identified patents, which patents are hereby incorporated herein by reference.

Other prior art bone-engaging substrate fastening means often employ several straight or curved cantilevered barbs, where the barbs may be elastically deformed to permit insertion into a hole drilled in a bone. These fasteners are well known in medical applications wherein the need for high holding strength has lead to the development of anchors having multiple cantilevered barbs. In any case, the body, the attachment means, and the bone-engaging means mechanically cooperate with one another to fasten a suture, bone portion, soft tissue, prosthesis, post or other substrate to a bone.

In the other embodiments of the prior art, expandable bone fasteners include a body and a plurality of barbs that are formed of material which may be elastically deformed from normal configuration to anchor to the bone tunnel. Such fasteners, however, generally lack an expansion pin and may be retracted only by drilling. These types of anchors may migrate and they are difficult to locate in the event they need to be removed.

Other prior art expansion pins, or functionally similar expansion pins having slidable elements used to expand the legs of the expandable bone fasteners, include a breakaway portion which is not implanted in the bone with the expandable bone fastener. On certain embodiments of the prior art expandable bone fasteners, tension must be applied to the expansion pin in order to expand the legs of the expandable bone fastener. It will, therefore, be understood by the artisan that anchoring devices, such as those taught in the above-referenced patents, generally comprise an anchor body, attachment means for attaching the desired object to the anchor body, and one or more barbs, pins, ridges, threads, or other bone-engaging means for holding the anchor body securely to the bone. Typically, the bone-engaging means is either manufactured separately from the body and then attached to the body by an assembly step, or is machined/milled from the body itself.

Accordingly, there remains a need for a fastener for securing tissue to bone which will have a predictable and sufficient initial anchorage strength to permit gradual load sharing to provide full repair and restoration of function of the tissue and bone. There exists a further need for a expandable bone fastener device having a novel expansion pin, which may be elastically deformed from normal configuration, wherein the outer ends of its barbs extend outwardly of the body toward a surrounding bone and to easily, rapidly and reliably anchored to the bone, as the expansion pin is retractable from a fully extended position. There exists a further need for an expandable bone fastener device that can be easily removed from the bone without the need for drilling in the event complications arise either during or after the surgery.

SUMMARY

In accordance with the present invention, expandable bone fasteners are provided which are operable for attaching either an autogenous substrate such as tissue, or an exogenous substrate such as a bone plate, to a bone. Embodiments of the expandable bone fasteners are adapted to meet the variety of demands presented by various surgical procedures employed during orthopedic, plastic and reconstructive surgery. The expandable bone fasteners of the present invention include absorbable, nonabsorbable and hybrid embodiments.

It is a first object of the invention to provide a device which may be used to attach a material substrate to a bone.

It is a further object of the invention to provide a bone fastener device which may be anchored securely in an untapped hole drilled in a bone.

It is another object of the invention to provide a bone fastener device meeting the above objectives which may be permanently implanted in a bone It is yet another object of the invention to provide a bone fastener device which will remain anchored in bone for a predetermined period of time after implantation.

It is yet a further object of the invention to provide a bone fastener device having barbs thereon and adapted to be inserted into a hole drilled in a bone, the barbs being expandable into the surrounding bone in various angles and positions with respect to the vertical axis of the hole, and retractable from the surrounding bone.

It is another object of the invention to provide an bone fastener adapted for insertion into a hole drilled into a bone, the bone fastener having an elongate body portion with a longitudinal axis, and an expansion pin slidably mounted within the body portion and having a plurality of barbs located in circumferentially spaced relation about the expansion pin and disposed to project radially outwardly from the body portion in various angles and positions with respect to the longitudinal axis to penetrate into the bone as the expansion pin is slidably retracted from within the body portion.

It is another object of the invention to provide an improved method for attaching a substrate to a bone.

It is yet a further object of the invention to provide a bone fastener, which may be non-absorbable, partially absorbable or totally absorbed by the body following implantation therein.

It is another object of the invention to provide a bone anchoring device comprising a plurality of expandable barbs, wherein the penetration depth of the barbs into surrounding bone is controllable.

It is yet another object of the invention to provide an expandable bone fastener adapted for insertion into a hole in a bone, thereafter to be expanded to provide non-releasable engagement between the expandable bone fastener and the wall of the hole.

The features of the invention believed to be novel are set forth with particularity in the appended claims. However the invention itself, both as to organization and method of operation, together with further objects and advantages thereof may be best understood by reference to the following description taken in conjunction with the accompanying drawings in which:

BRIEF DESCRIPTION OF THE DRAWINGS

FIG. 9 is a partially cutaway elevational view of an expandable bone fastener insertion tool operable for inserting the tubular outer body of a top loading expandable bone fastener into a hole drilled in bone and for forcing a top loading expansion pin into the axial bore of the tubular outer body.

FIG. 10 is a schematic left end view of the expandable bone fastener insertion tool of FIG. 9.

FIG. 11 is a right end view of the expandable bone fastener insertion tool illustrated in FIG. 9.

FIG. 12 is a side elevational view of an expansion pin insertion rod adapted for use with the expandable bone fastener insertion tool of FIG. 9.

DESCRIPTION OF THE PREFERRED EMBODIMENTS

Figure 1:
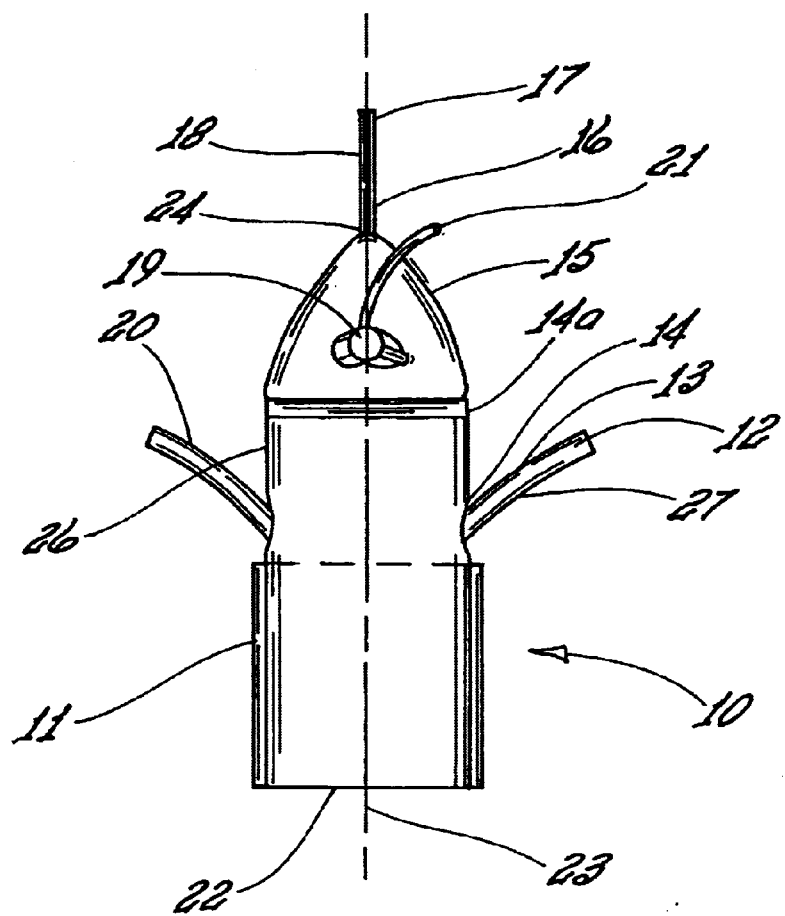
FIG. 1 is a perspective view of the expansion pin comprising an expandable bone fastener in accordance with the present invention.

Turning now to FIG. 1, an expansion pin 10 comprising the expandable bone fastener 30 (FIG. 4) of the present invention has a longitudinal axis 23, proximal head portion 15, a distal end 22 and a body portion 26 therebetween. Expansion pin 10 of the expandable bone fastener 30 has at least two identical barbs 20 and 27 projecting elastically outward from the body portion 26. The two identical barbs 20 and 27 are curved in their normal unstressed state and have a sharp distal point 12, a curved section 13 and are attached to the body portion 26 at joint 14. The proximal head portion 15 of the expansion pin 10 has a suture hole 19 therein, and the distal end 22 of the body portion 26 has longitudinal guiding track 11 on the outer surface thereof.

The expansion pin 10 has an elongate core 18, preferably a length of metallic wire, having proximal end 17 and a distal end 16. The distal end 16 of core 18 is surrounded by a conical portion 15 having an abrupt shoulder 24 on proximal end thereof. The joint 24 between the conical portion 15 and the core 18 comprises a frangible structural material, which is different from structural material comprising the core 18, and is most preferably a bioabsorbable material.

Figure 2:
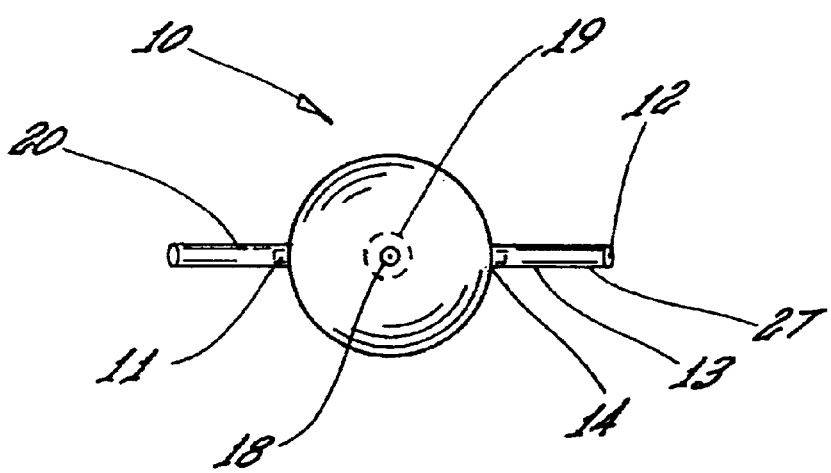
FIG. 2 is a proximal end view of the expansion pin illustrated in FIG. 1.

Referring next to FIG. 2, which is an end view of the proximal end of the expansion pin 10 illustrated in FIG. 1, the plurality of elastically deformable barbs comprising expansion pin 10, two of which are indicated at 20 and 27 in FIG. 2, are located in spaced circumferential relation to each other about the outer surface of the body portion 26 of expansion pin 10. The barbs 20 and 27 of expansion pin 10 may be affixed to the body portion 26 at either the same or different longitudinal positions with respect to the vertical axis 23 of expansion pin 10.

Figure 3:
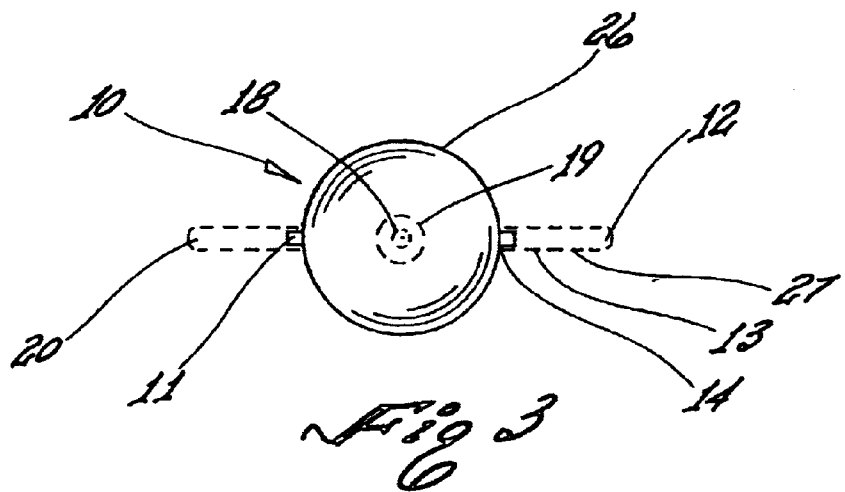
FIG. 3 is an end view of the distal end of an expansion pin wherein the expansion pin has a plurality of curved barbs extending outwardly from a body portion.
Figure 4:
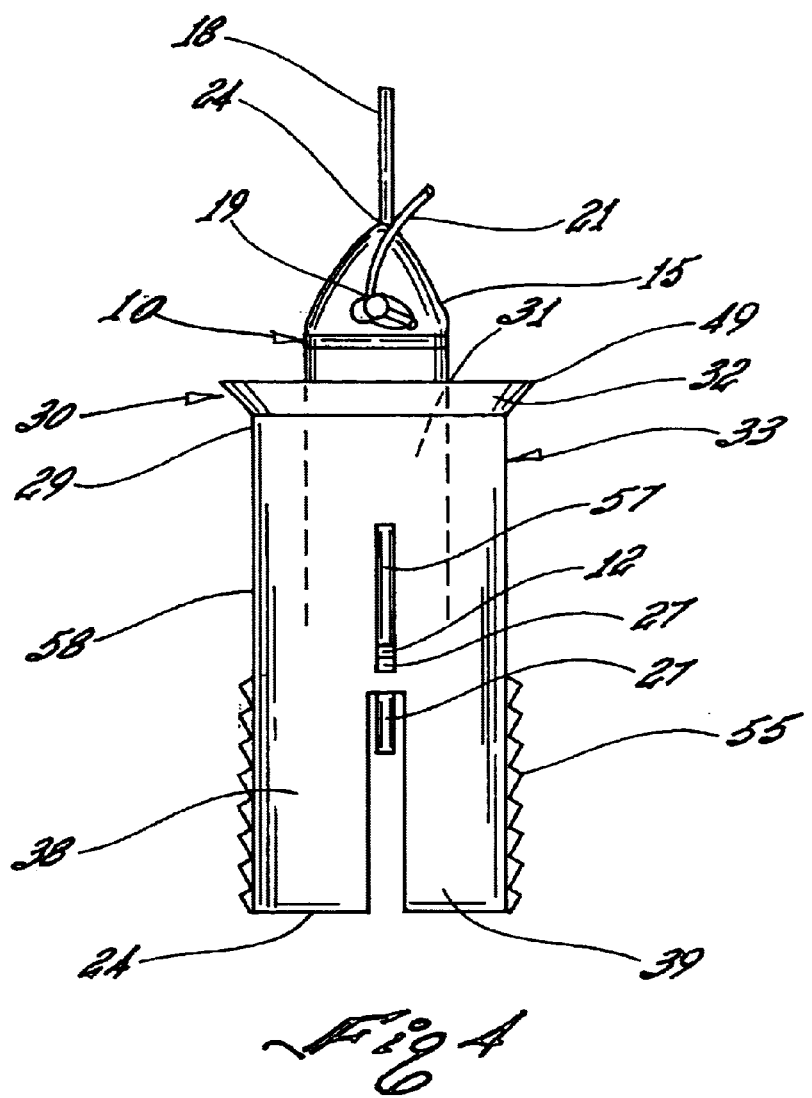
FIG. 4 is a perspective view of an expandable bone fastener of the present invention.

FIG. 3 is an end view of the distal end of an expansion pin 10 adapted to be slidably mounted within the outer tubular outer body member 33 (FIG. 4) to form an expandable bone fastener 30 in accordance with the present invention. With reference now to FIG. 4, the expandable bone fastener 30 comprises an outer tubular member 33 with expansion pin 10 slidably disposed within an axial bore 31 in the outer tubular member 33. The expandable bone fastener 30 has a proximal end 29, a distal end 34 and a tubular outer body portion 33 therebetween. The tubular outer body portion 33 of the expandable bone fastener 30 has an interior cylindrical bore 31 coextensive with the length thereof. The outer surface of the tubular outer body 33 of the expandable bone fastener 30 preferably includes bone stabilizing means such as annular barbs 55 that provide positive attachment of the outer tubular body 33 to the bone during insertion of the expansion pin 10. The conical head 15 of the expansion pin 10 includes a frangible joint 24 between the core 18 of the expansion pin 10 and the conical portion 15, and a suture hole 19 therein to permit the attachment of a suture 21 thereto.

Figure 5:
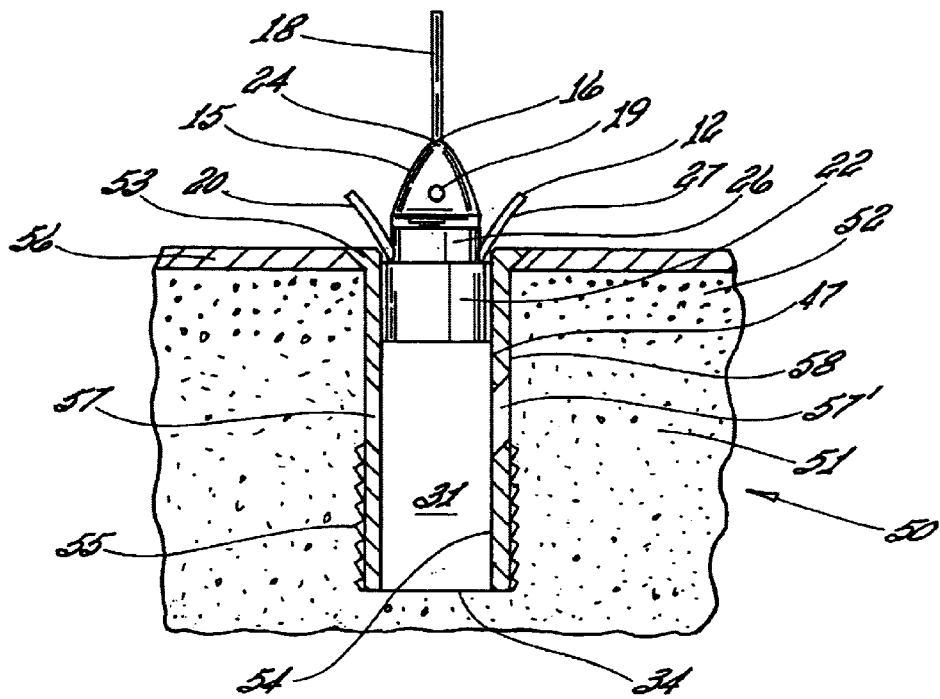
FIG. 5 is a cross sectional view of a top-loading embodiment of the expandable bone fastener of FIG. 4 disposed within an untapped hole drilled in a bone, shown in the early stage of inserting the expansion pin into the tubular outer body of the fastener.
Figure 6:
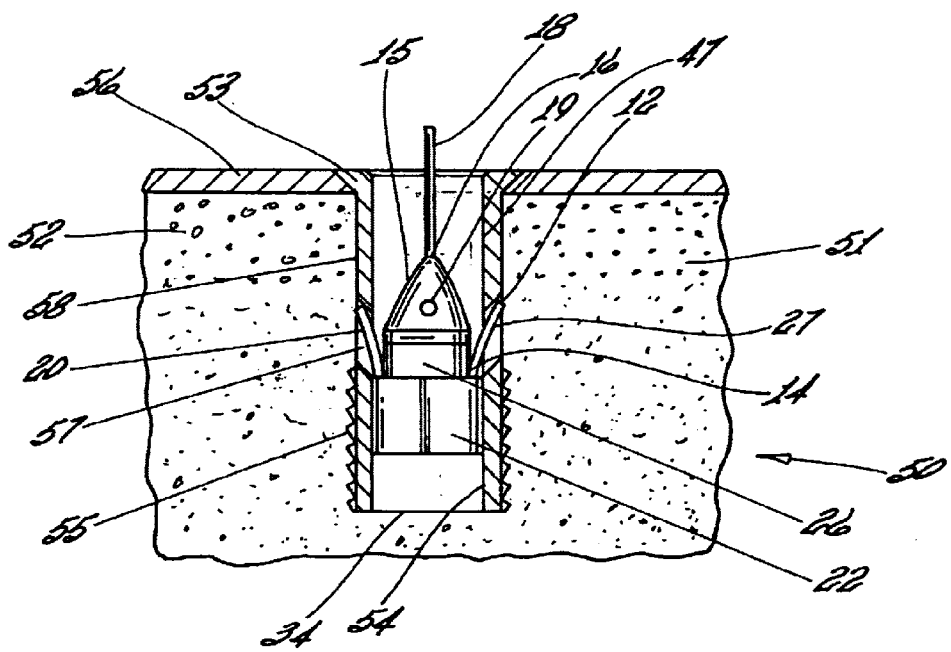
FIG. 6 is a cross sectional view of the top-loading expandable bone fastener illustrated in FIG. 5, shown in final stage of inserting of expansion pin into the tubular outer body of the fastener.

In order to use a top loading, non expandable legs type of bone fastener 30 in accordance with the present invention, a hole is first drilled in a bone at a site where a substrate such as bone plate is to be attached. The outer tubular body 33 of the expandable bone fastener 30 is inserted into the hole. With reference to FIGS. 5 and 6, the expandable bone fastener 30 can be used to attach a bone plate 56 to the bone. The proximal end of the outer body portion 33 of the expandable bone faster 30 has a taper 53 that match the taper of countersunk holes in the bone plate 56. The core 18 of the expansion pin 10 is dimensioned to slidably fit within the axial bore 31 of the tubular outer body 33 of bone fastener 30. A longitudinal groove on the wall of the axial bore 31 (not shown in FIGS. 5 and 6) is dimensioned to fit snugly to the mating guiding track 11 of the expansion pin 10. The barbed portion of the expansion pin 10 is depressed by the application of external pressure to the core 18 and slidably guided down through the axial bore 31 to the distal end of the tubular outer body 30 axial bore 54. As the barbed portion of the expansion pin enters the axial bore, barbs 20 and 27, which barbs are formed out of an elastically deformable material, are forced radially inwardly so as to be disposed entirely within the axial bore 31 of the outer tubular member 33. When the distal end 16 of the core 18 enters the axial bore, the barbs 20 and 27 are adjacent to slots 57 and 57' and the sharp ends 12 of the barbs 20 and 27 expand into the slots 57 and 57'. The elongated core 18 is then pulled upwardy and as the sharp outer ends 12 of the barbs 20 and 27 encounter the upper (proximal) edge of the slots 57 and 57'. the barbs are forced progressively outwardly thereby penetrating the cancellous bone 51. As the elongated core 18 is progressively pulled upwardly in a proximal direction, the sharp outer ends 12 of the barbs 20 and 27 enter the cortical bone 52. Further traction of the elongated core 18 causes the frangible joint 24 to break, thereby separating the core 18 of the expansion pin 10 from the conical portion 15 thereof. To remove the embedded expandable bone fastener from the bone, a pushpin similar to the elongated core 18 is inserted into the proximal end of axial bore 31 to contact the conical portion 15 of the expansion pin at the proximal end thereof. The expansion pin is forced in a distal direction until the distal end 22 of the expansion pin touches the distal end 34 of the tubular outer body 33. In this fully depressed position, the barbs 20 and 27 are retracted through the slots 57 and 57' from within the surrounding bone 51 and folded in the axial bore 31. The expandable bone fastener 30 may then be removed from the hole by applying traction to the expanded proximal end of the tubular outer body 33.

Figure 7:
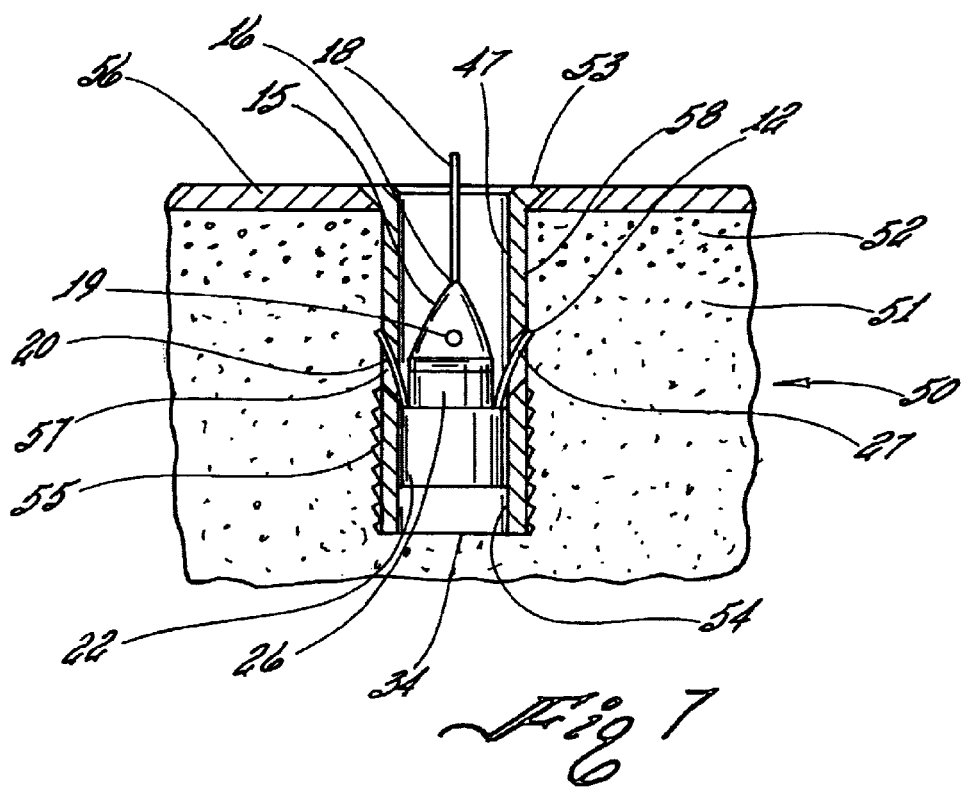
FIG. 7 is a cross sectional view of a rear-loading embodiment of an expandable bone fastener in accordance with FIG. 4, shown in early stage of inserting the expansion pin into the axial bore of the tubular outer body.
Figure 8:
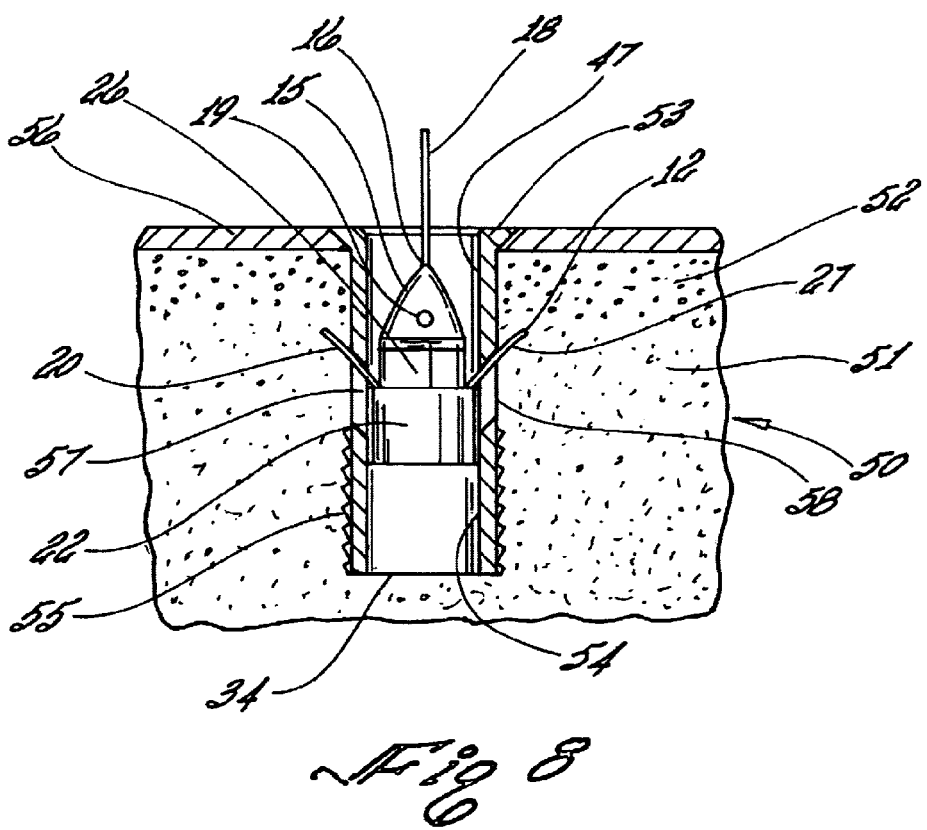
FIG. 8 is a cross sectional view of the rear-loading expandable bone fastener illustrated in FIG. 7, shown with the barbs expanded in the final stage of locking the expandable bone fastener in the bone by moving the expansion pin through the axial bore of the tubular outer body in a proximal direction.

In order to use a rear loading embodiment of an expandable bone fastener in accordance with the present invention, as with the top loading embodiment, described above, a hole is first drilled in a bone at a site where a substrate such as bone plate is to be attached. The distal end 16 of the core 18 of the expansion pin 10 is fully inserted into the tubular outer body 33 until the barbs are substantially confined to lie within the axial bore 31 with the sharp end 12 of the barbs 20 and 27 disposed either adjacent to or distal to the slots 57 and 57'. The distal end 34 of the tubular outer body 33 is inserted into the hole and advanced thereinto until the expanded head 49 (FIG. 4) is adjacent the bone plate 54 or bone. With reference to FIGS. 7 and 8, the rear loading embodiment of the present bone fastener 30 is illustrated being used to attach a bone plate 56 to a bone 51. The expanded proximal end of the 49 of the tubular outer body 33 has a taper 53 that matches the taper of a hole in the bone plate 56. As the elongated core 18 is pulled upwardly in a proximal direction, the sharp outer ends 12 of the barbs 20 and 27 are forced outwardly and upwardly until the sharp ends 12 pierce the cortical bone 52 thereby anchoring the bone fastener 30 within the hole and the bone plate 56 to the bone. As with the top loading embodiment, continued traction applied to the core 18 separates the core 18 from the conical portion 15 of the expansion pin 10 at the frangible joint 24. In the event the need should arise, the bone fastener 30 may be removed from the hole with the assistance of a push pin in the manner described above for the top loading embodiment.

In the preferred embodiment, barbs 20 and 27 are formed out of polymer blends of glycolide and/or lactide homopolymer, copolymer and/or glycolide/lactide copolymer and polycaprolactone copolymers, and/or copolymers of glycolide, lactide, poly (L-lactide-co-DL-lactide), caprolactone, polyorthoesters, polydioxanone, trimethylene carbonate and/or polyethylene oxide or any other bioabsorbable material. A pseudoelastic shape memory alloy of the type disclosed in U.S. Pat. No. 4,665,906 entitled "Medical Devices Incorporating SIM Alloy Elements", issued May 19, 1987 to Jervis, which patent is specifically incorporated herein by reference. By way of example, one such pseudoelastic shape memory alloy might be a nickel titanium alloy such as Nitinol, which is available from Flexmedics of Minneapolis, Minn., among others. The use of such a material, in combination with the normal orientation of the barbs relative to the anchor body, permits the barbs to initially deflect inwardly to the extent required to permit the anchor to move forward in the bone tunnel, yet still resiliently "spring back" toward their normal, outwardly projecting position so as to prevent the anchor from withdrawing back out the bone tunnel.

A tool useful for inserting a top-loading expandable bone fastener 30 in accordance with the present invention into a hole drilled in a bone is shown in elevational cross-sectional view at 70 in FIG. 9 and front and rear end views in FIGS. 10 and 11 respectively. The tool 70 has a distal bone fastener-grasping end 71 and a proximal end 72 and a barrel 73 there between having an axial bore 74 dimensioned to slidably accommodate the proximal end of the core comprising the expansion pin therewithin. With the proximal end of the tubular outer body 33 of the top-loading expandable bone fastener 30 held securely within the distal end 71 by suitable bone fastener grasping means, the distal end 34 of the expandable bone fastener is inserted into a hole drilled in a bone. Squeezing rotatably mounted trigger 75 forces the expansion pin 10 into the axial bore 31 of the outer tubular body 33 comprising the top-loading expandable bone fastener 30. When the trigger 75 is released, a spring (not shown) retracts the core thereby expanding barbs 20 and 27 into the surrounding bone. The expanded proximal end of the expandable bone fastener 30 is released when the trigger 75 returns to its initial position. As discussed earlier, in the event that the body portion 26 of the expansion pin 10 is bioabsorbable and the core 18 is metallic, the tool 70 includes means adapted to apply tension to the proximal end 17 of the core 18, following barb expansion, in a quantity sufficient to separate the core 18 from the body portion 26.

While particular embodiments of the present invention have been illustrated and described, it would be obvious to those skilled in the art that various other changes and modifications can be made without departing from the spirit and scope of the invention. For example, the legs of the outer tubular member 33 can be either expanded or remain undeformed when the expansion pin is advanced into the axial bore 31 of the outer tubular member 33 in a distal direction. Similarly, the outer surface of the outer tubular member is disclosed as cylindrical in the preferred embodiment, but may be hexagonal or have another polygonal cross sectional profile. It is therefore intended to cover in the appended claims all such changes and modifications that are within the scope of this invention.

What I claim is:

1. An expandable bone fastener for fixation within a hole drilled in a bone comprising:
    (a) an outer tubular body having an expanded proximal end, a distal end, an elongate body portion therebetween and an axial bore, the body portion having an outer surface with a plurality of longitudinal slots therein; and
    (b) an expansion pin comprising an elongate core having a proximal end and a distal end, and an elongate body portion having a proximal end attached to said distal end of said core at a frangible joint, and a distal end, said body portion having an outer surface with a barbed portion comprising at least two elastically deformable barbs disposed in circumferentially spaced relationship with respect to an adjacent barb, extending outwardly from said outer surface;

wherein when said barbed portion of said expansion pin is disposed within said axial bore of said outer tubular member, said barbs project into said slots of said outer tubular member.

2. The expandable bone fastener in accordance with claim 1 wherein said body portion includes a longitudinal ridge on said outer surface thereof, and wherein said axial bore of said outer tubular member has a longitudinal groove on a surface thereof, said longitudinal groove being dimensioned to slidably accommodate said longitudinal ridge therewithin.

3. The expandable bone fastener in accordance with claim 1 wherein said expandable bone fastener further comprises substrate fastening means affixed thereto, said substrate fastening means being operable for attaching a substrate to said expandable bone fastener.

4. The expandable bone fastener in accordance with claim 3 wherein said substrate fastening means is a suture hole disposed on said proximal end of said body portion.

5. The expandable bone fastener in accordance with claim 3 wherein said substrate fastening means is said expanded proximal end of said outer tubular member.

6. The expandable bone fastener in accordance with claim 1 wherein said body portion of said tubular outer member has a plurality of legs on said distal end thereof.

7. The expandable bone fastener in accordance with claim 1 wherein said expandable bone fastener comprises a bioabsorbable, moldable polymer.

8. The expandable bone fastener in accordance with claim 1 wherein said expandable bone fastener comprises a pseudoelastic shape memory alloy.

* * * * *